United States Patent [19]
Kline et al.

[11] Patent Number: 5,392,032
[45] Date of Patent: Feb. 21, 1995

[54] APPARATUS FOR SENSING WET DIAPER INCLUDING CIRCUIT BREAKER

[75] Inventors: Michael J. Kline, Pittsburgh; Paul A. Pottgen, Allison Park; Neil J. Szuminsky, Pittsburgh, all of Pa.

[73] Assignee: Little Acorn Ventures, Pittsburgh, Pa.

[21] Appl. No.: 158,120

[22] Filed: Nov. 23, 1993

[51] Int. Cl.⁶ ............................................. G08B 21/00
[52] U.S. Cl. .................... 340/604; 128/886; 604/361; 340/573
[58] Field of Search ............. 340/603, 604, 605, 573; 200/61.04, 61.05; 604/361; 128/886

[56] References Cited
U.S. PATENT DOCUMENTS

| | | | |
|---|---|---|---|
| 4,163,449 | 8/1979 | Regal | 340/604 X |
| 4,356,479 | 10/1982 | Wilson | 340/604 |
| 4,539,559 | 9/1985 | Kelly et al. | 340/573 |
| 4,754,264 | 6/1988 | Okada et al. | 340/573 |
| 4,800,370 | 1/1989 | Vetecnik | 340/573 |
| 5,036,859 | 8/1991 | Brown | 340/573 X |
| 5,197,958 | 3/1993 | Howell | |
| 5,264,830 | 11/1993 | Kline et al. | 340/604 |

Primary Examiner—Jeffery A. Hofsass
Attorney, Agent, or Firm—Michael J. Kline

[57] ABSTRACT

A device for signaling a wet condition in a diaper (12). The device includes a sensing means (10) for sensing wet conditions in the diaper (12) and signal means (15) connected to the sensing means (10) for producing a signal substantially concurrently with sensing the wet conditions in the diaper (12). The sensing means (10) are insulated from the wearer when the diaper (12) is dry and are activated by the diaper (12) once the diaper (12) becomes wet.

20 Claims, 8 Drawing Sheets

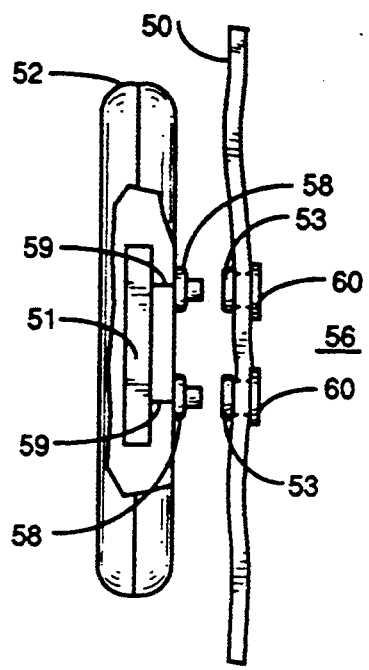
FIG. 7
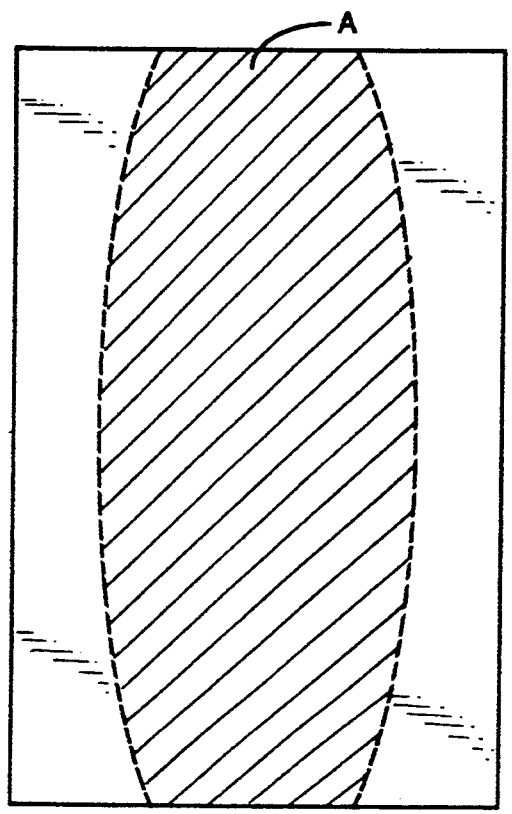
FIG. 9
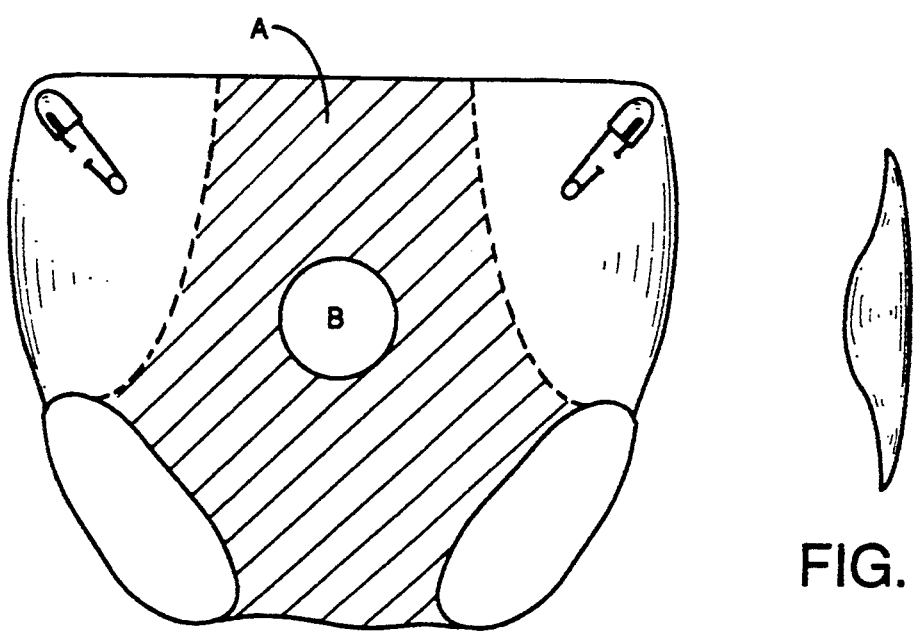
FIG. 8
FIG. 10

APPARATUS FOR SENSING WET DIAPER INCLUDING CIRCUIT BREAKER

FIELD OF THE INVENTION

The present invention relates to devices used to sense wetness, particularly to devices sensing wet conditions in a diaper.

BACKGROUND OF THE INVENTION

In the past several years, environmental concerns have caused a growing number of parents and other caretakers to revert to the use of cloth and/or cotton diapers rather than disposable diapers; however, in that they do not wick urine or other bodily fluids away from the skin of the wearer, rather tend to envelop the entire surface of the wearer's skin contacting the diaper with the urine or other bodily fluid. These conditions can go unnoticed for several hours or more, exposing the wearer's skin to the harsh and irritating affects of urine and other bodily fluids. A condition commonly known as "diaper rash" may result, making it especially critical that those in charge of caring for the diaper wearer are alerted to the diaper's wet condition as soon as possible, to minimize the wearer's exposure to irritating fluids.

Various treatments have been devised for minimizing diaper rash, including the application of waterproof creams and jellies to the wearer's skin. While such treatments tend to shield the wearer's skin from wetness, they have the distinct disadvantage in precluding the passage of air to the skin, generally recognized as an essential component of the healing process. Thus, it is not uncommon for diaper rash to persist in a chronic or near chronic state for several weeks and even months.

The problem is further compounded for diaper wearers who are in institutional environments, such as day care centers, mental institutions, convalescent homes, hospitals and so on, wherein a number of other diaper wearers are simultaneously cared for. As a practical matter, it is not possible for those providing care to such individuals to constantly check each and every diaper wearer on a frequent basis.

A number of attempts have been made in the past to address wet undergarments. Kelly et al., U.S. Pat. No. 4,539,559 discloses a sensing circuit which uses an adhesive strip and clamp or pin to fasten the sensor to the diaper or the garment being sensed for wetness. The sensor includes a pair of wire electrodes running the length of the adhesive strip. One problem with this device is that the adhesive becomes less and less adherent with each application, due to the wetness of the diaper environment and/or the tendency to pick up lint, dirt, etc., which lessens adhesive strength and compromises reusability. Additionally, there is an obvious aversion to placing wire electrodes of any type in close proximity with small children. Indeed, Kelly et al. concedes that the device is not intended for small children. Kelly et al. is also inconvenient, suggesting that, the electrodes could be mounted on the cloth diaper, for example, with printed circuits on the cloth or by sewing the electrodes into the diaper. Such mounting seriously impairs the ability to reuse the device, since cloth diapers are frequently handled by diaper services and subjected to harsh chemical and/or thermal disinfectant procedures. Kelly et al. also contemplates using a faint alarm, audible only to the wearer, which of course, is of little use to an infant.

Accordingly, a significant advance in the art could be realized if a device could be developed that would alert the caretaker of the diaper wearer of a wet situation in the diaper. The apparatus must be small enough to not interfere with the wearing comfort of the diaper, yet must not be readily swallowed by the wearer, who could choke on the device. Additionally, the device must be sensitive enough to alert the caretaker as soon as possible following the diaper becoming wet.

Accordingly, it is an object of the invention to provide a device for quickly signaling to those caring for a diaper wearer of the diaper becoming wet;

It is another object of the invention that the signal shall be audible and/or visual;

It is yet another object of the invention that the device can be worn comfortably and not interfere with the function of the diaper itself;

It is another object of the invention that the device in no way jeopardize the health or safety of the wearer.

These and other objects of the invention shall become more readily apparent as the following detailed description of the invention proceeds.

SUMMARY OF THE INVENTION

The invention comprises a sensing device which is sensitive to the wet conditions of a diaper almost immediately upon the diaper becoming wet. As used herein, the term "diaper" is broadly construed to mean cloth diapers (e.g., cotton diapers), disposable diapers of all kinds, training pants, whether made of cotton or other material, and all diaper-like devices used for incontinent adults as well as children and animals.

As used herein, the term "diaper wearer" includes infants, adults, animals, and any other living creature on which a diaper may be applied.

The present invention utilizes an alarm which is preferably positioned on the outside surface of the diaper so as not be in direct contact with the wearer's skin. When used in connection with a cloth diaper, the device is preferably either attached directly to the external surface of the diaper, or most preferably is attached to the waterproof or plastic pants placed over the cloth diaper.

When used in connection with a disposable diaper, the device is preferably positioned in an embedded location within the diaper, yet remains separated from the internal surface of the diaper so as not to come in direct contact with the wearer's skin.

The device preferably includes an audible alarm which is triggered when the diaper becomes wet. In one embodiment of the invention, the audible alarm comprises a small battery-powered alarm connected through an electrical circuit having a pair of spaced contacts. The spaced contacts keep the circuit open as long as the diaper is dry and as soon as the portion of the diaper in immediate contact with the spaced contacts becomes wet, the wetness of the diaper bridges the spaced contacts, which completes the circuit, and sounds the alarm.

In another embodiment of the invention the audible alarm is either replaced with or augmented with a visual alarm which may signal, for example, through a blinking light, that the diaper has become wet. Such an alarm is preferably mounted in a position on the external surface of the diaper in a location which is readily viewed by the caretaker, such as on the front portion of the diaper.

In one preferred embodiment of the invention, the device comprises a relatively thin disk having a pair of spaced contacts facing the diaper. The disk is preferably positioned in a fixed relationship on or sealed inside the waterproof pants, such as on the front section of the pants in the pubic region, positioned anterior relative to the wearer upward of the genitalia. This positioning is least likely to interfere with the comfortable wearing of the diaper and least likely to result in injury to the wearer. Because the device is positioned on the external surface of the diaper, the diaper itself assists in cushioning of the wearer from the device should the wearer fall on the device while wearing it.

BRIEF DESCRIPTION OF THE DRAWINGS

A full understanding of the invention can be gained from the following description of the preferred embodiments when read in conjunction with the accompanying drawings in which;

FIG. 7 is a schematic representation, top elevation view, partially broken away, of a preferred embodiment of the invention.

FIG. 8 is a schematic representation of a diaper, showing the region most likely to experience wetness.

FIG. 9 is a schematic representation of a diaper, laid flat, showing the region most likely to experience wetness.

FIG. 10 is a side elevation of a preferred embodiment of the invention.

DETAILED DESCRIPTION OF THE PREFERRED EMBODIMENTS

Figure 1:
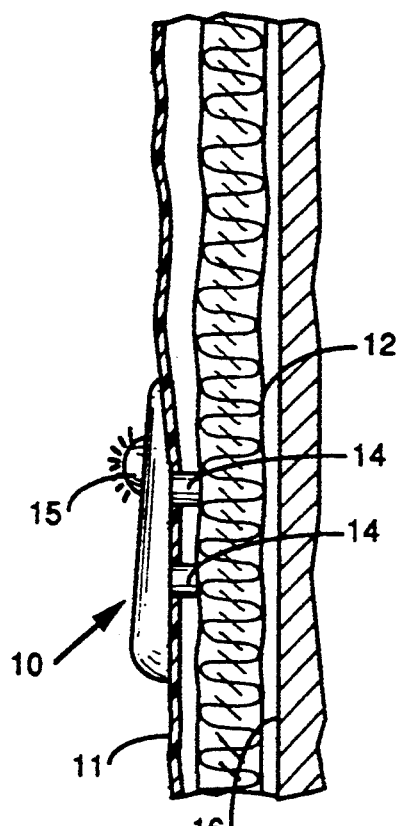
FIG. 1 is a schematic representation, in partial cross-section, of a preferred embodiment of the invention.
Figure 2:
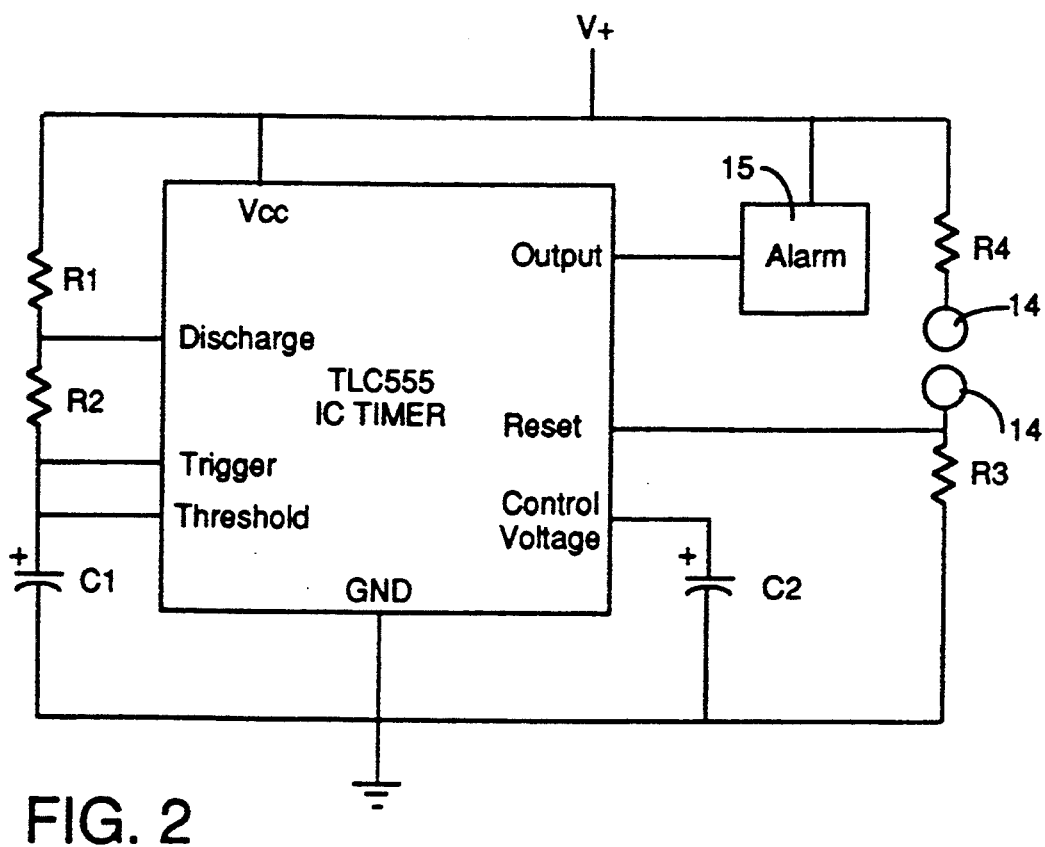
FIG. 2 is a circuit diagram of a preferred embodiment of the invention.
Figure 3:
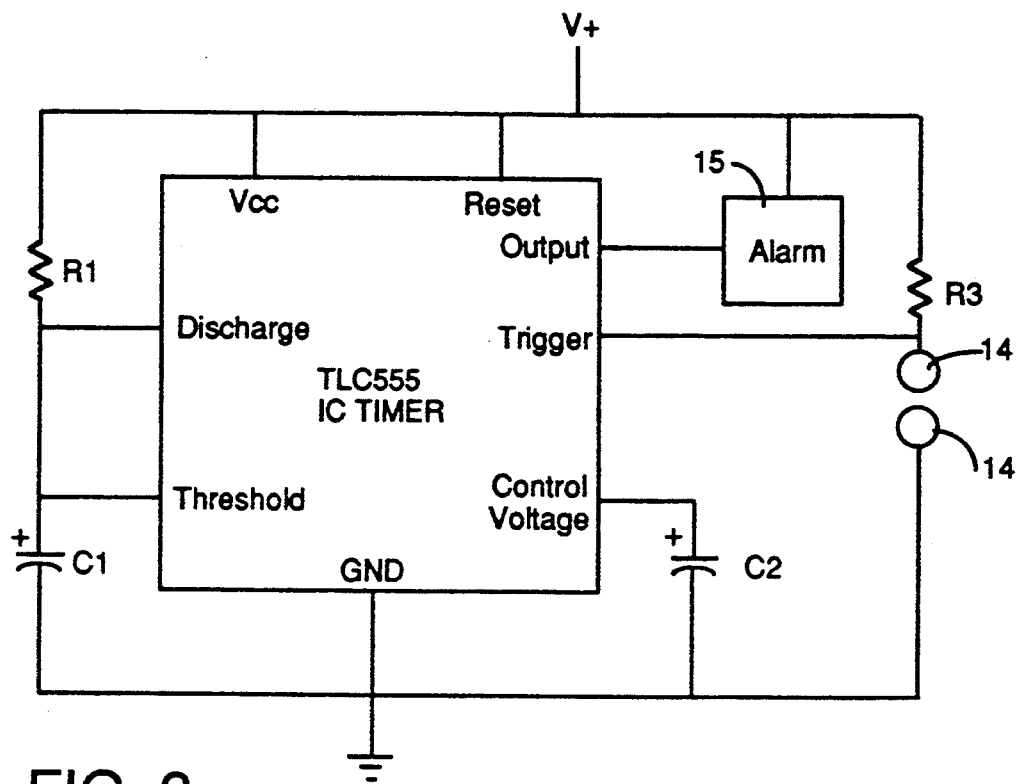
FIG. 3 is a circuit diagram of a preferred embodiment of the invention.

Referring to FIG. 1, there is illustrated a wetness sensing device of the invention, generally 10, fastened to a pair of waterproof pants 11 covering a diaper 12. As used herein the term "waterproof pants" is intended to mean rubber pants, plastic pants, and any polymeric or water resistant material covering a diaper, whether a disposable diaper or a cloth diaper, for purposes of retaining wetness within the diaper and away from the wearer's outer clothing.

As illustrated in FIG. 1, the outer layer 11, which may be waterproof pants, assists in pressing a pair of electrical contacts 14 into contact with the diaper 12. Additionally, the wearer's outer clothing may assist in pressing the contacts 14 in contact with the diaper 12. When the diaper 12 becomes wet these contacts 14, which are spaced apart, are bridged by the wetness within the diaper and able to complete a circuit which sounds an alarm 15 within the sensing device 10. The sensing device 10 produces an audible signal substantially simultaneously with the sensation of wetness between the contacts 14.

As illustrated in FIG. 1, it is preferred that the sensing device be positioned such that there is never any chance of the electrical contacts 14 touching the wearer's skin 16 facing the inside of the diaper 12. As an added precaution, the device 10 is powered with a battery having sufficiently low voltage to insure no risk of electrical shock to the wearer. Generally, a three-volt battery is sufficient to sound the audible alarm 15 and at the same time preclude any risk of electric shock. As long as the diaper 12 remains dry, it acts as an electrical insulator, preventing the contacts 14 from being bridged by the wearer's skin 16.

Figure 4:
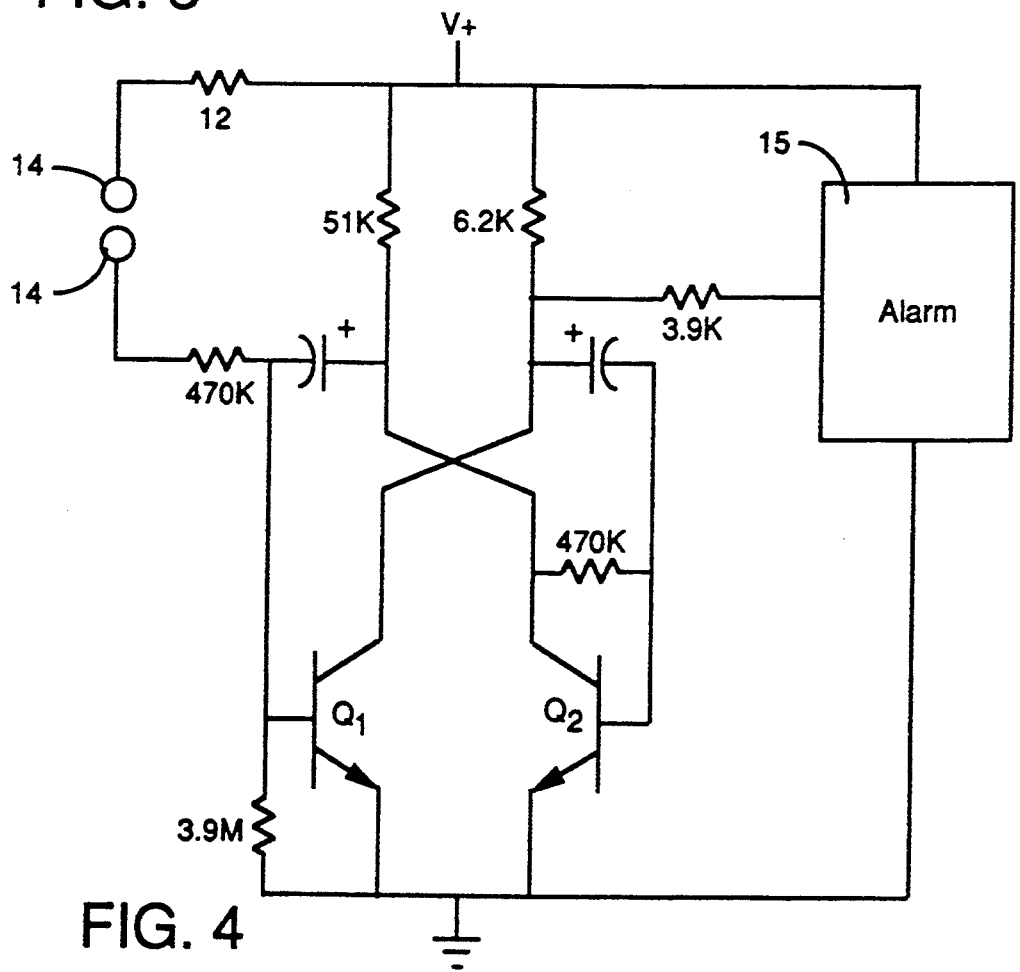
FIG. 4 is a circuit diagram of a preferred embodiment of the invention.
Figure 5:
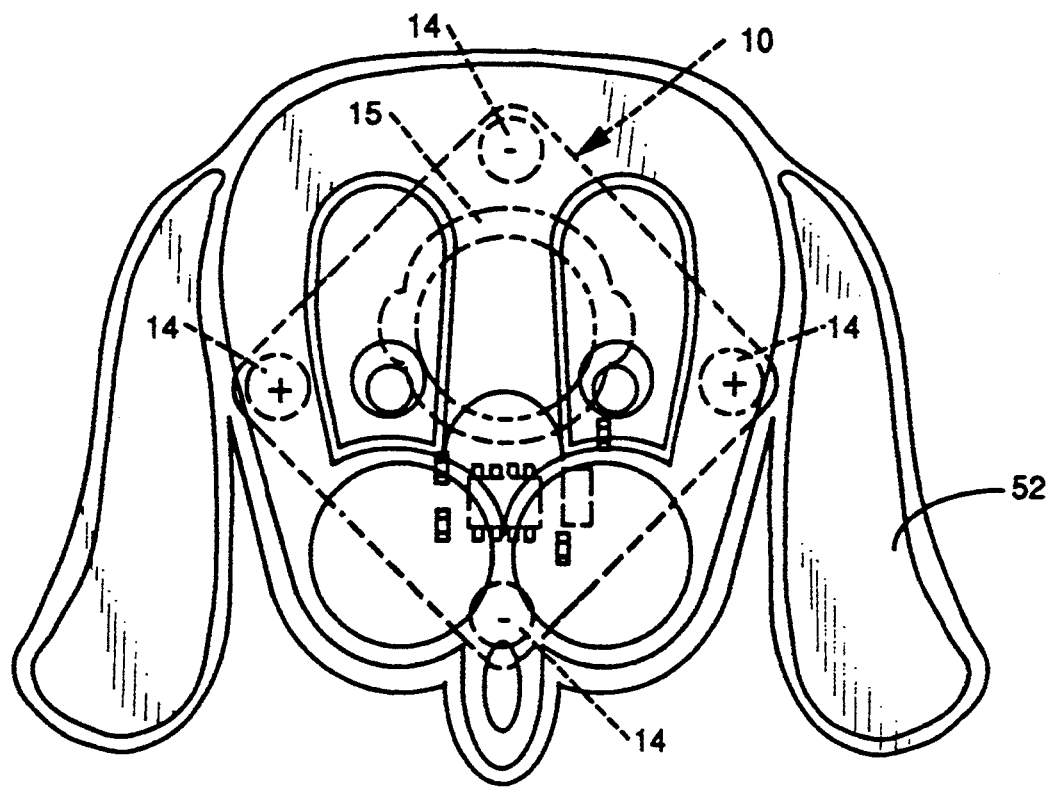
FIG. 5 is a schematic illustration of a preferred embodiment of the invention.

The spaced contacts 14 of the device 10 as illustrated in FIG. 1 comprises a pair of electrical point configured. A representative flexible circuit with component outlines is shown in various shades of grey. Superimposed is an outline of a resilient applique 52 that acts as a cushioning layer over the circuit. The device may be held to the diaper cover by four conducting snaps 14. In the representation of FIG. 4, the snaps are arranged at the four corners of the flexible circuit in such a way as to optimize the area monitored for moisture, the snaps 14 doubling as spaced electrical contacts.

Figure 6:
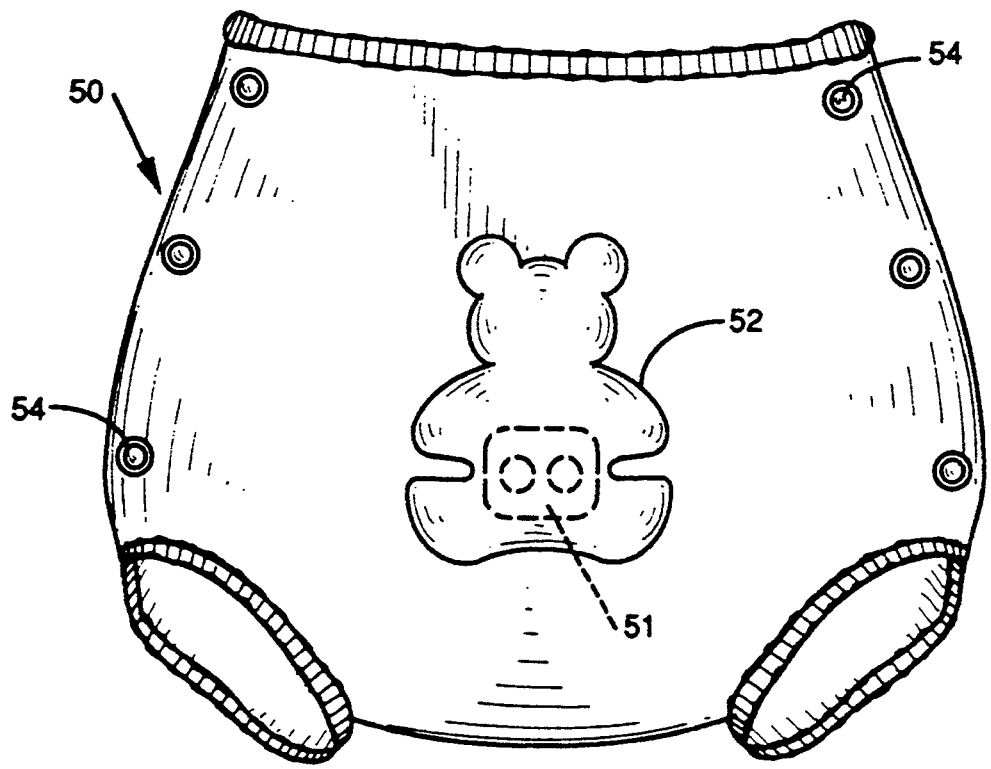
FIG. 6 is a schematic illustration of a preferred embodiment of the invention.

A highly preferred embodiment of the invention is shown in FIGS. 6 and 7. In this embodiment, diaper cover 50 include the sensing device 51 contained within an externally mounted cushioning means, 52, which may be formed into a decorative shape. The cushioning means may utilize various foam rubbers or foam polymers, or other cushioning materials to insure that the sensing device 51 causes no wearing discomfort. The cushioning means 52 is sufficiently sized so as not to be capable of being swallowed by small children or others wearing the device. In this embodiment, the audible portion of the device is not significantly muffled by the cushioning means, which may be covered with a fabric or other sound-permeable material.

As seen in FIG. 7, which is a top plan elevation of the FIG. 6 embodiment, the spaced electrical contacts may preferably be a part of the means for attaching the sensing device to the waterproof diaper cover 50. As shown, a pair of snaps, 53, are punched through the wall of the diaper cover 50 without compromising the waterproof integrity of the diaper cover 50. This type of snap is known in the art of plastic pants, which traditionally have used such snaps for fastening the sides of waterproof pants together with side snaps 54 illustrated in FIG. 6. Because the snaps 53 are conductive, they can sense wetness on the internal side of the plastic pants, 56. These snaps 53 receive a complementary snap 58, as illustrated. While snaps 53 as illustrated comprise female connectors and snaps 58 are male connectors, the relative positions of the male and female connectors can readily be reversed as will now be appreciated.

The snaps 58 are electrically connected via leads 59 to the sensing circuit housed in the sensing device 51. Thus, when the snaps 53 and 58 are engaged, the internal surface 60 of the snaps 53 become spaced electrical contacts of the invention, capable of sensing wetness when bridged by a wet diaper.

Because the snaps 53 maintain an essentially watertight seal with respect to the diaper cover 50, there is no requirement that the cushioning means 52 be waterproof, although it is, of course, preferred that the cushioning means 52 is waterproof. The entire device 51 contained by the cushioning means 52 can be conveniently unsnapped to allow washing of the plastic diaper cover 50.

Virtually any location of the diaper is likely to experience wetness from urine being passed by the wearer of the diaper. Of course, the greater the quantity of urine passed, the greater the area of the diaper experiencing wetness. We have generally found that the area of the diaper most likely to experience wetness immediately after urination corresponds to the area A shown in dotted lines and shaded in FIGS. 8 and 9. This area corresponds to a region of the diaper covering a band extending from roughly the naval to the pubic bone, the genitalia, the anus and the coccyx, or tail bone of the wearer.

While the most preferred location on the diaper for sensing wetness is the region immediately adjacent the urethra, this location also corresponds with a sensitive area of the wearer. Accordingly, we have found it preferable, from the standpoint of wearer comfort, to place the sensing device above the urethra, anterior on the wearer, in a location roughly corresponding to the pubic bone, seen as region B on FIG. 8. We have found that this location is least likely to interfere with the wearer's comfort, whether standing, walking or sitting. In crawling infants, it may be desirable to position the device posteriorly, roughly near the coccyx. By placing the device on the exterior surface of the diaper, the diaper itself cushions the wearer from the device, contribution to added wearer comfort.

Tests have shown, surprisingly, that the diaper need not be wringing wet to initiate the signalling device. When spaced contacts are used for the sensing device, even a slightly damp condition is sufficient to bridge the contacts and signal wetness. Of course, the contacts are more likely to be bridged by a wetter diaper, which coincides with a more serious condition requiring more immediate attention from the caretaker.

We have also found that the location of the device in this position, on the diaper's exterior and near the pubic region, permits the sensing device to signal wetness very shortly following urination, generally less than a minute. This is especially true in cloth/cotton diapers, which tend to absorb fluids quickly.

In another preferred embodiment of the invention, the sensing device, which may comprise a disk, is fitted with a collar which snaps into place at a predetermined location on the waterproof diaper cover, and may be removed for washing. In yet another embodiment, the device is positioned with a pocket in the waterproof diaper cover which may be sealed and opened for removal of the device for washing. In still another embodiment of the invention, the device is permanently sealed in the waterproof diaper cover. In yet another embodiment, as previously discussed, a pair of conductive snaps double as the spaced contacts and as the fastening means for removably securing the device to the waterproof diaper cover.

The audible alarm 15 in FIGS. 1–5, may comprise a buzzer, beeper, bell, or any audible signal, such as a song, which will alert the caretaker to the wet diaper situation. A recognizable tune would be especially useful in situations where multiple diaper wearers are being cared for, and each wearer could be given a diaper having a different tune to better indicate which diaper has just become wet.

The device of the invention may either be disposable or reusable and may preferably be packaged in a water-resistant or watertight/waterproof housing.

Ordinarily, the spaced contacts will be in direct contact with the diaper, as previously discussed. This direct contact may be augmented with an adhesive, such as VELCRO®, glue, snaps, conductive tape, or other fastening devices to further insure that the spaced contacts remain in direct contact with the diaper at all times during which the diaper is worn.

In a highly preferred embodiment of the invention, the housing of the device is fabricated of a semi-rigid material that is flexible around the edges, but more rigid toward the spaced contacts. Suitable materials include a wide array of polymers, silicones, foams, paddings, etc.

In one embodiment of the invention, the housing of the device is galaxy-shaped, the outer edges tapering from the thicker hub position, as shown in FIG. 10.

Depending on the polymer used, the housing of the sensing device may be watertight, capable of being washed in a conventional washing machine. In this embodiment, all of the electronics are preferably potted within the device, except for the sensing portion of the device, which must be exposed to the diaper and wet conditions. While the signal of the device may also be sealed within the housing, a preferred embodiment uses an audible signaling device having an exposed surface that is resistant to corrosion by body fluids, and is sealed in watertight fashion in the device.

When the device is used in an institutional setting or other environment in which a relatively large number of diaper wearers are cared for by a relatively smaller number of caretakers, it may be desirable, from a privacy standpoint, that an audible alarm not be used. Rather, it may be advantageous for the signal to include a transmitter which transmits a signal of wet conditions in the diaper to a remote location, font example, to a monitor, which is capable of identifying the wearer whose diaper has generated the signal.

The battery of the device can be easily checked by simply bridging the contacts with the caretaker's finger prior to placement on the wearer.

The device can also sense wet conditions other than urination, for example, sensing when the wearer has had a wet stool, such as diarrhea, which bridges the contacts and sounds the alarm, or such as when the wearer has spilled a non-body fluid, such as a drink on the diaper.

It is important that the device of the invention sense wetness, and not produce a false signal when the diaper is dry. Such a false signal could be produced should the electrical, spaced contacts of the device come into direct contact with the wearer's skin such that the spaced contacts are closed and the electrical circuit is completed, producing the false signal. Accordingly, it is preferred that the electrical spaced contacts of the invention be positioned relative to the diaper in a way that keeps the contacts electrically insulated from the wearer so long as the diaper remains dry. We have found that the diaper itself acts as an insulator when dry and only completes the electrical connection when wet. The necessary electrical insulation is readily achieved by positioning the spaced contacts on the external surface of the diaper relative to the wearer. Of course, it would also be possible to partially embed the spaced contacts within the diaper, such as in a disposable diaper, provided there is sufficient diaper or other insulating material between the spaced contacts and the wearer to preclude any false signals caused by the wearer completing the circuit.

In another preferred embodiment of the invention, the battery used to power the signal means comprises a pair of different metal electrodes (such as zinc/copper) capable of generating a potential when contacted by urine. Because urine is an electrolytic solution, it can be used as a component of the battery. When such a battery is used, it is possible to eliminate the spaced contacts, as the battery is only able to generate current for the signal upon being wetted by the urine. It may, however, be desirable to keep a pair of spaced contacts in the circuit, which would permit the device to be re-used on a dry diaper even if the battery remained powered from the previous wetting incident.

A most highly preferred embodiment of the invention is illustrated in FIGS. 11-20. In this embodiment, the wetness sensing circuit includes a power interrupt for preventing battery drain by the circuit when the sensing device is not being used. This power interrupt disconnects the battery from the circuit when the housing containing the sensing device is unfastened from the diaper cover, for example, during washing of the diaper cover.

Figure 11:
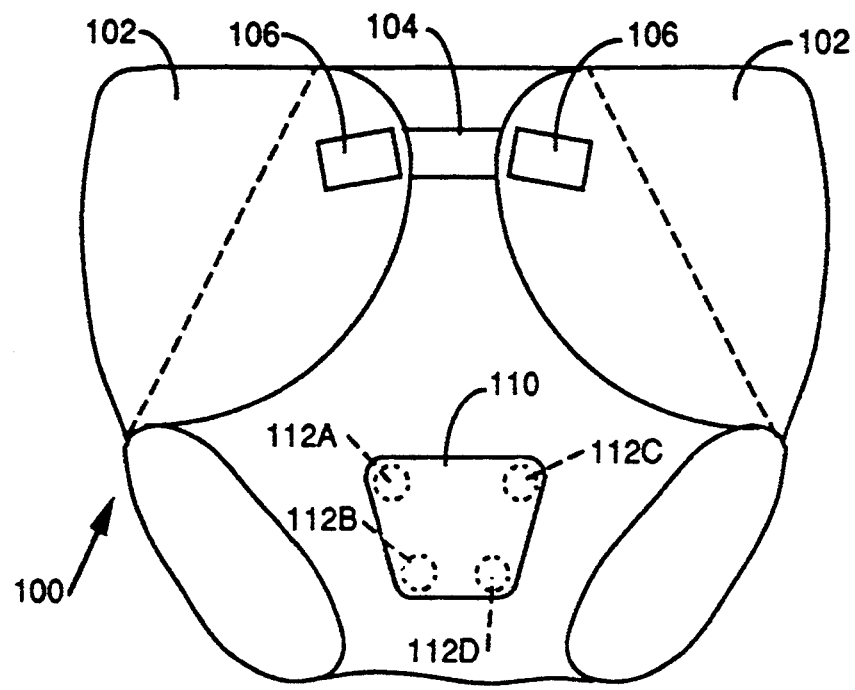
FIG. 11 is a schematic elan view of a preferred diaper cover of the present invention.

FIG. 11 illustrates a diaper cover generally (100) which may, for example, comprise a cover having flaps (102) which fold over the wearer and are fastened to the front portion of the cover (104), for example, with velcro strips (106). As illustrated, a preferred wetness sensor (110) may have a generally trapezoidal shape in order to maximize the area of wetness being sensed while facilitating user comfort. In the embodiment of FIG. 11, four spaced electrical contacts (112A-D) are employed.

Figure 12:
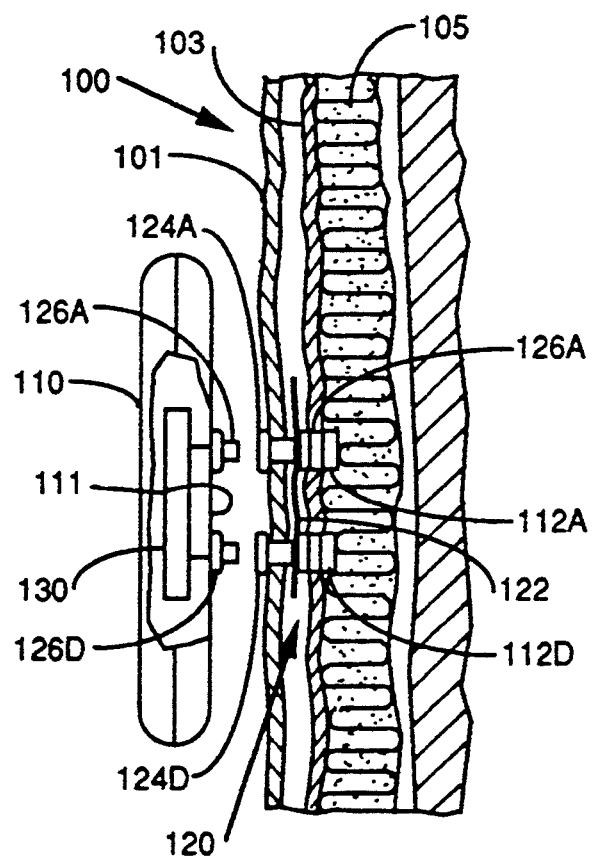
FIG. 12 is a cross-sectional side view of a portion of the diaper cover of FIG. 11.

Referring to FIG. 12, the diaper cover (100) includes an outer surface (101) and an inner surface (103). The inner surface (103) contacts the absorbent diaper (105). The absorbent diaper (105) may comprise a cloth diaper, or synthetic disposable diaper material known to those of ordinary skill in the art. The inner surface (103) of the diaper cover (100) may comprise an absorbent material such as natural or synthetic fibers, while the outer surface (101) of the diaper cover (100) is preferably a waterproof material known to those of ordinary skill in the art.

Figure 13:
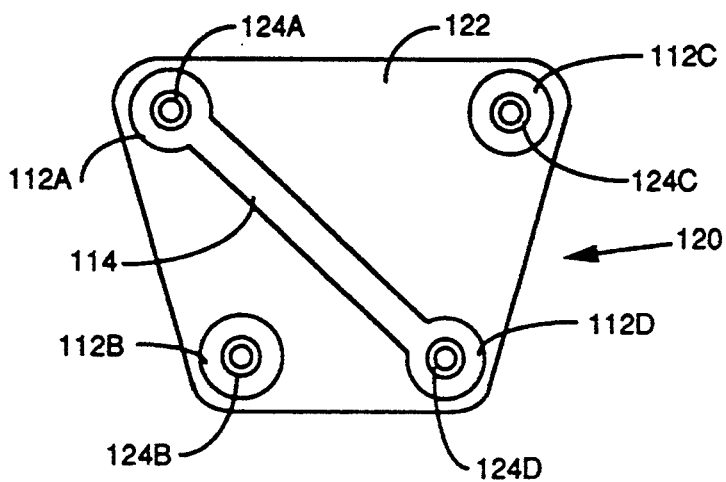
FIG. 13 is a schematic plan view of a preferred circuit breaker device of the present invention.

The diaper cover (100) preferably includes a power interrupt device generally (120) positioned internally within the diaper cover (100) between the outer and inner layers (101), (103) respectively. This power interrupt (120) is best illustrated in FIG. 13, and comprises a generally planar flexible material, such as plastic (122) through which the spaced electrical contacts (112A-D) are placed. In the embodiment of FIG. 13, two electrical contacts (112A) and (112D) are bridged with a conductive material (114), which may comprise conductive tape, conductive ink, conductive cloth, wire, or any other suitable conductive material known to those of ordinary skill in the art. The conductive material (114) should be flexible to compliment the flexibility of the planar member (122).

Referring again to FIG. 12, the spaced electrical contacts (112A) and (112D) are positioned internally with respect to the inner surface of the diaper cover (103) such that these contacts press against the diaper (105). The contacts (112A) and (112D) in turn pass through the inner layer (103) of the diaper cover (100) and are fastened to the flexible member (122), for example, by riveting, welding, press fitting, or any other attachment procedure known to those of ordinary skill in the art. It is critical that the electrical contacts (112A-112D) remain electrically connected to the power interrupt (120) and wetness sensor (110) as will now be described.

The outward side of the flexible member (122) includes fastening members (124) which are electrically conductive and permit electrical contact between the spaced electrical contact (112A-D) to which each is connected. This is achieved, for example, by passing the fastening device (124A) through a small hole in the flexible member (122) and fastening same to a metal rivet (126A) on the opposite side of the flexible member (122), the metal rivet (126A) in turn passing through the inner surface (103) of the diaper cover (100) and contacting the diaper (105). The fastening members (124A-124D) preferably comprise metal snaps or other fastening devices known to those of ordinary skill in the art, including hooks, conductive velcro, clasps, or any other fastening device that can provide an electrically conductive connection. As illustrated in FIG. 12, each fastening device (124A-124D) has a complimentary fastening device (126A-126D) positioned on the sensing device (110). In the embodiment of FIG. 12, these complimentary fastening devices comprise metal snaps (126A-D). These snaps (126A-D) in turn are electrically connected to the wetness sensing and signalling circuit substantially as previously described.

Figure 14:
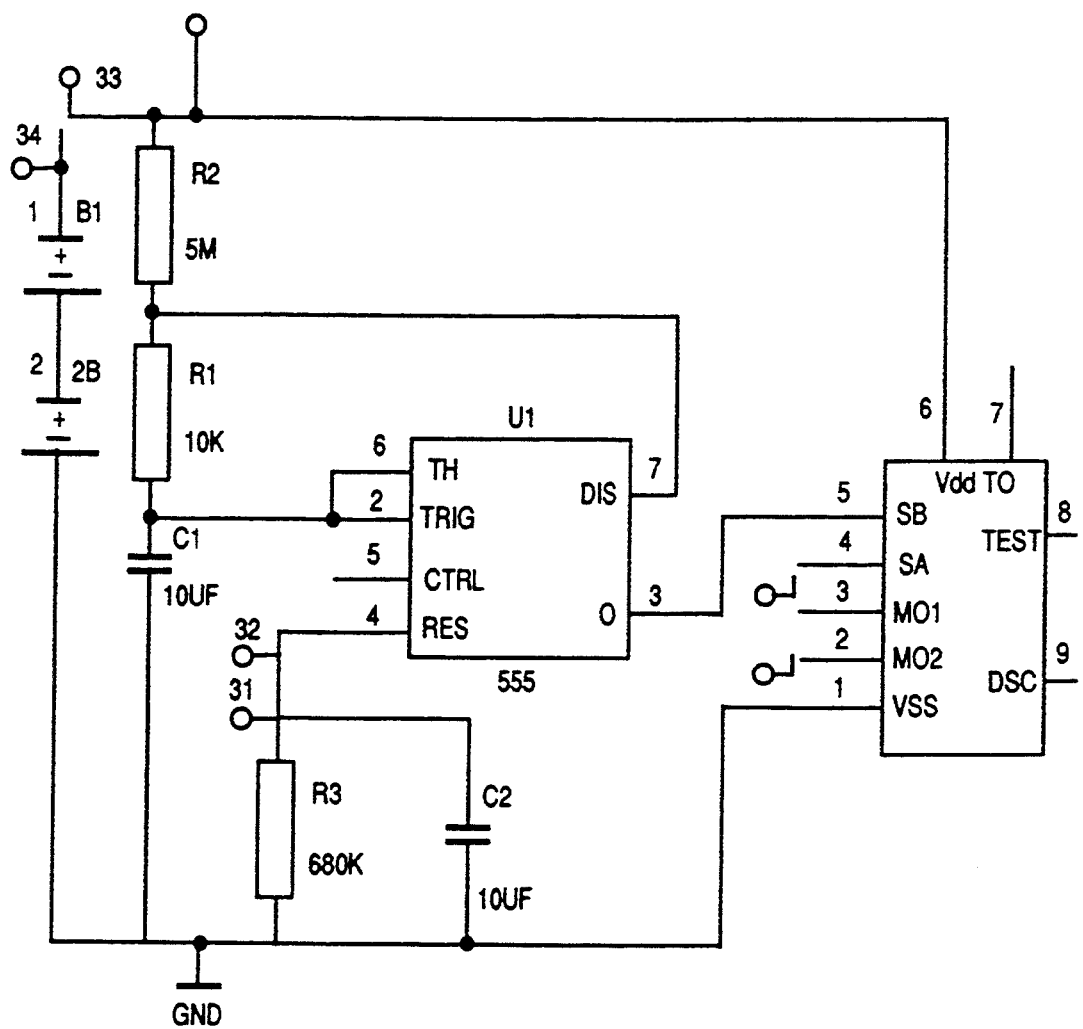
FIG. 14 is a schematic circuit diagram of a preferred wetness sensing circuit of the present invention.

FIG. 14 illustrates a schematic circuit diagram incorporating the power interrupt of the present invention. As illustrated, one or more batteries (B1, B2) power the circuit, which is connected to a signal device at J5–J6. When the power interrupt (120) of FIG. 13 is snapped to the sensing device (110), snaps (124A) and (124D) come into electrical contact with the complimentary snaps (126A) and (126D), respectively, bridging the circuit at J3–J4 of FIG. 14 through the conductive material (114). When the sensing device (110) is unsnapped from the diaper cover (100), this breaks the circuit at J3–J4, disconnecting the batteries B1 and B2 and thereby preventing battery drain. When the circuit is bridged at J3–J4, the spaced electrical contacts, J1, J2 in FIG. 14, are able to complete the sensing circuit, sounding an alarm between J5–J6 once the leads J1, J2 are bridged electrically, for example, with a conductive fluid.

The alarm connected to leads J5–J6 may be, in addition to a visual or audible alarm, a vibrational alarm which silently alerts the wearer of a wet condition in the diaper. Such vibration may be achieved, for example, by a solenoid or a small electric motor having an eccentric weight.

The alarm circuit is completed and the alarm sounds whenever either of the electrical contacts connected to the leads J1 or J2 is bridged by wetness between any other spaced contact, such as those connected to the leads J3, J4. Thus, the device of FIG. 13 senses a relatively wide area on the diaper.

The sensing device (110) includes a housing as previously described. It is preferred that at least the inner surface (111) of the sensing device (110), and particularly that portion between the electrically conductive fastening devices (126A–D) be of a water resistent material. Otherwise, if the surface (111) becomes wet, the electrical connection between (126A and 126D), for example, remains bridged until the surface (111) dries which, for absorbent materials can be quite some time.

Figure 15:
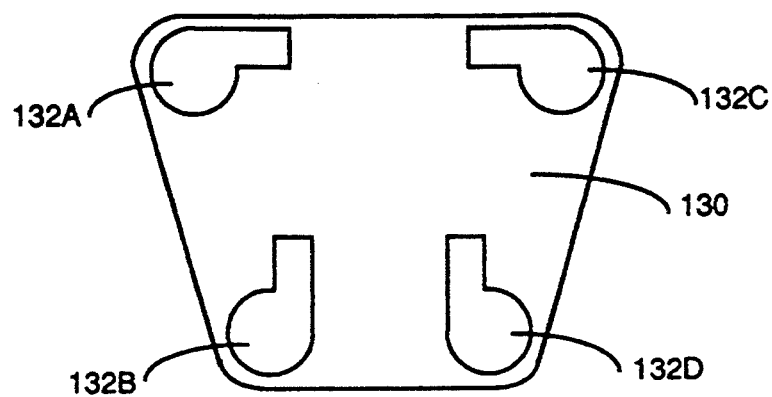
FIG. 15 is a schematic illustration of a flexible backing for mounting a printed circuit board useful in practicing the present invention.
Figure 16:
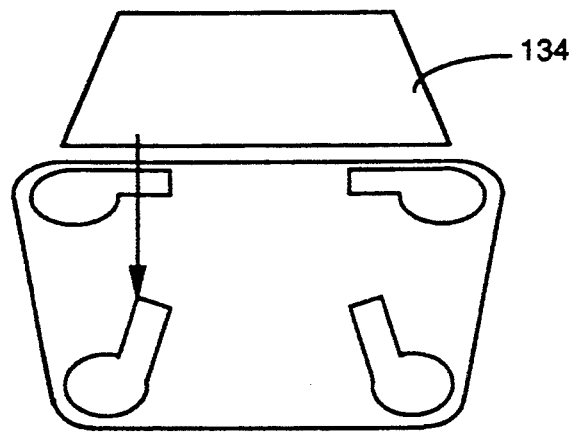
FIG. 16 is an isometric view illustrating how a printed circuit board of the present invention may be mounted to the backing of FIG. 15.
Figure 17:
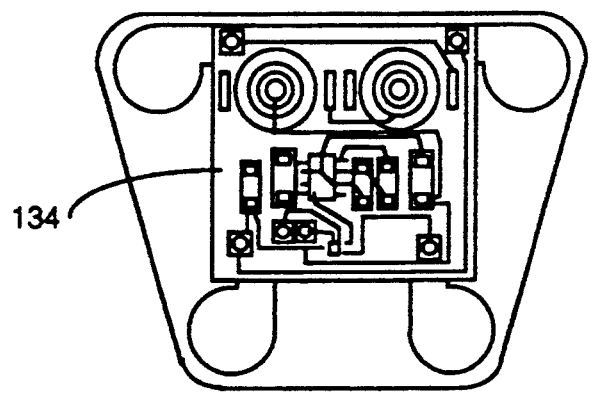
FIG. 17 is a schematic plan view showing the printed circuit board mounted to the backing of FIG. 15.

FIGS. 15–17 illustrate how a printed circuit board comprising the circuit of FIG. 14 may be connected to a flexible layer within the housing of the sensing device (110). A flexible material (130) which may be the same as that of 122 previously described, is fabricated with electrically conductive material (132A–D) at the corners. A printed circuit board (134) including the circuit of FIG. 14 is placed onto the flexible material (130) and electrically attached to the conductive material (132A–D). This electrically conductive material (132A–D) may be electrically conductive tape, electrically conductive ink, electrically conductive fabric, as previously described. When the power interrupt device of FIG. 13 is used, in combination with the circuit of FIG. 14, lead J3 is electrically connected to (132A) or (132D) and lead J4 is connected to the other of (132A) or (132D). Lead J1 is connected to either (132B) or (132C) and lead J2 is connected to the other of (132B) or (132C).

Figure 18:
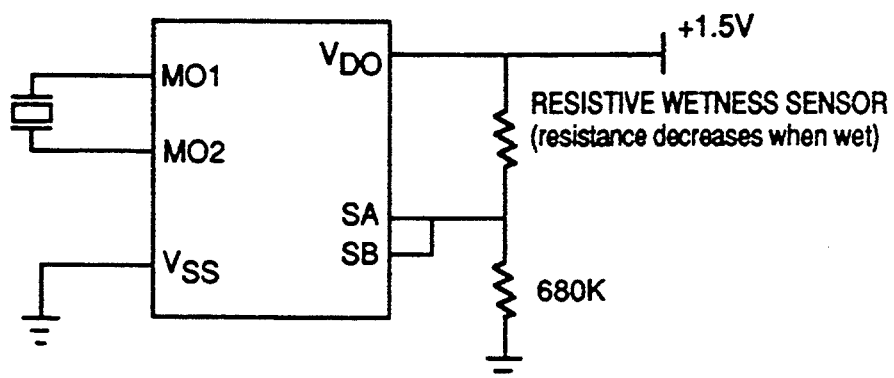
FIG. 18 is a schematic circuit diagram illustrating a semi-conductor chip useful in practicing the present invention.
Figure 19:
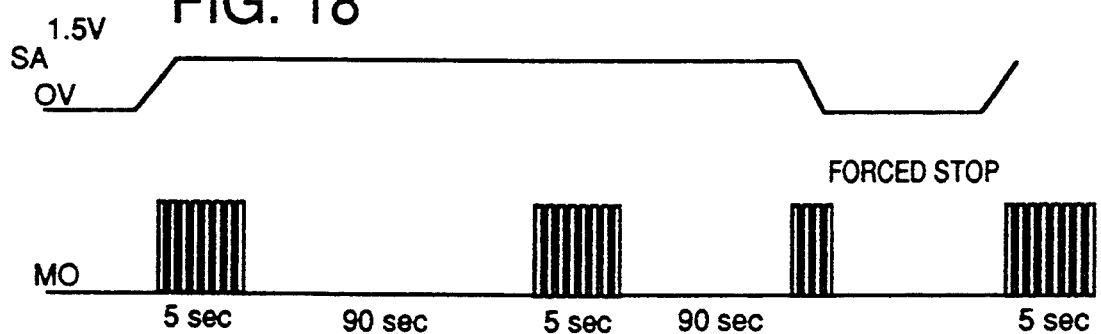
FIG. 19 is a schematic diagram illustrating a preferred timing sequence of the present invention as utilized by a semi-conductor chip such as illustrated in FIG. 18.
Figure 20:
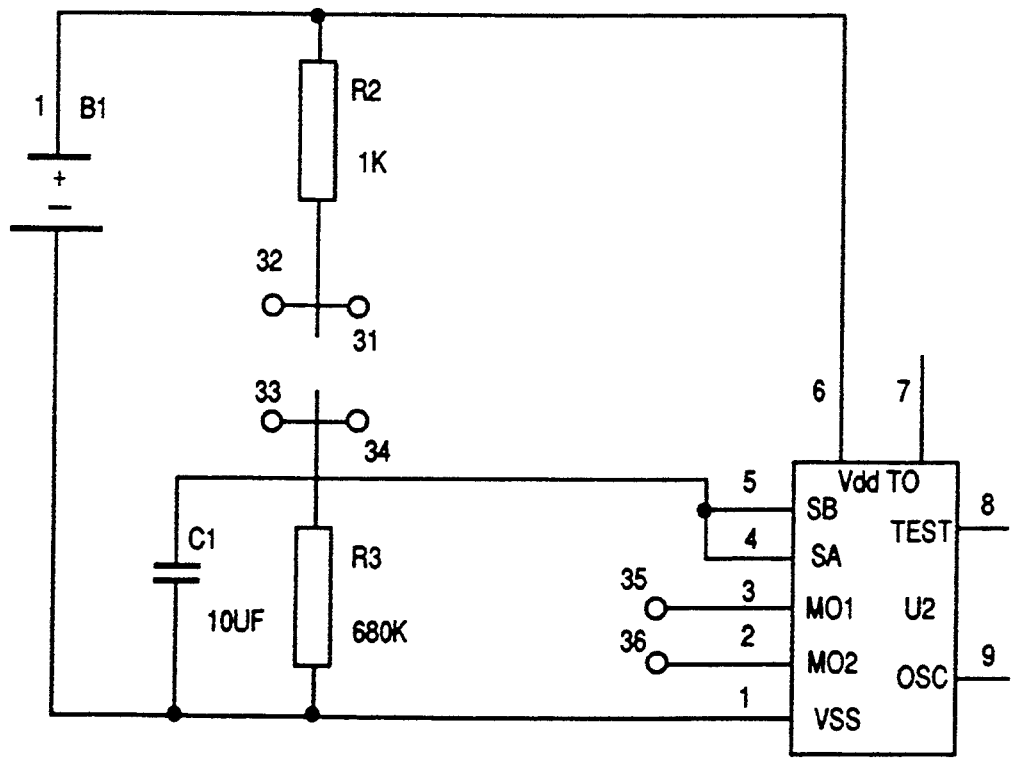
FIG. 20 is a schematic circuit diagram illustrating a wetness sensing circuit using a semiconductor chip such as that illustrated in FIG. 18.

Of course, the circuit of FIG. 14 need not be embodied on a printed circuit board, but may be entirely embodied on a semi-conductor chip. A suitable chip includes the HM5801 by Hualon Microelectronics Corporation, Taipei, Taiwan ROC, modified such that when triggered the sound chip sounds for a short period of time (e.g., 5–10 seconds) and then remains silent for a longer period of time (e.g., 80–90 seconds), repeating that cycle as long as the wetness sensor remains wet. FIG. 18 illustrates schematically the sound chip as modified and FIG. 19 illustrates schematically a timing diagram illustrating a preferred timing mode for the chip. An advantage of using a chip such as that described is decreased size of the sensor and decreased power consumption, enabling a single battery B1 to be employed as illustrated in FIG. 20. The leads J1, J2, J3, J4, J5, J6, are connected to the sensing circuit substantially as previously described.

It will now be readily appreciated that the present invention may be used to advantageously sense wet conditions on items other than diapers, including, without limitation, surgical dressings, bed coverings, clothing, skin, etc. Also, it should now be understood that bodily fluids of all types can be sensed, initiating the signal produced by the invention, including, without limitation, urine, blood, saliva, sweat, vomitus, mucus, semen, tears, milk, feces, and water, all of which are electrolytic in varying degrees.

It is also contemplated to be within the scope of our invention that the sensing device can be built into diaper pins used to pin a cloth diaper to the wearer. While such a use has the advantage of requiring no modification to existing diapers or waterproof diaper cover, a disadvantage is that the location of the pins, on the sides of the wearer, does not generally correspond to an area of the diaper most likely to experience wetness, except in cases of the wearer passing large volumes of urine, or where multiple urination episodes are experienced by the same diaper.

The invention may be used for a variety of applications. In addition to quickly alerting a caretaker that an individual within their care has discharged a bodily fluid, the device may be used in conjunction with urine receptacles positioned within the diapers for catching urine for analysis. In is frequently desirable to perform bacterial analysis, such as a bacteria count, on such collected samples, and the results may be skewed if the urine sits for long periods and bacteria multiply. The invention enables the immediate retrieval of collected samples before such bacterial growth proliferates.

We claim:

1. A waterproof diaper cover including means for sensing wet conditions in a diaper with which said waterproof diaper cover is in contact, said waterproof diaper cover having fastened thereto a wetness sensing means having a signal means connected thereto, said wetness sensing means electrically connected to a pair of spaced contacts positioned internally with respect to said waterproof diaper cover such that said spaced contacts are in contact with a diaper being worn by a wearer of said waterproof diaper cover, said sensing means and signal means being housed within housing means secured to said waterproof diaper cover, wherein said spaced contacts comprise fastening means for fastening said housing means to said diaper cover, said signal means being powered by battery means, said fastening means including power interrupt means for preventing battery drain when said housing means is unfastened from said diaper cover.

2. The device of claim 1 wherein said signal is audible.

3. The device of claim 1 wherein said signal is visual.

4. The device of claim 1 wherein said signal is vibrational.

5. The diaper cover of claim 1 wherein said diaper is a cloth diaper, said sensing means being secured to said diaper cover in a location generally corresponding to a location on said diaper likely to experience wetness from the wearer of said diaper.

6. The diaper cover of claim 1 wherein said diaper is a disposable diaper.

7. The device diaper cover of claim 1 wherein said sensing means senses the presence of bodily fluids passed into said diaper by a wearer of said diaper.

8. The diaper cover of claim 1 wherein said signal means includes transmitter means for transmitting said signal to a location remote from a wearer of said diaper cover.

9. The device of claim 8 wherein said transmitter means transmits said signal to a monitor means, and said monitor means is adapted to identify the wearer of the diaper cover transmitting said signal.

10. The diaper cover of claim 2 wherein said signal means includes amplifier means allowing said audible signal to be heard by persons caring for a wearer of said diaper cover.

11. The waterproof diaper cover of claim 1 wherein said signal means comprises an audible indicator.

12. The waterproof diaper cover of claim 1 wherein said housing means comprises cushioning means housing said wetness sensing and signal means, and said housing is removably fastened to the front side of said waterproof diaper cover on the exterior thereof, substantially over the pubic bone region of a wearer of said waterproof diaper cover.

13. The diaper cover of claim 7 wherein said bodily fluid comprises an electrolytic solution and said sensing means includes battery means, said battery means providing sufficient voltage to initiate said signal means upon being wetted by said electrolytic solution.

14. The diaper cover of claim 13 wherein said electrolytic solution is selected from the group consisting of urine, blood, saliva, sweat, vomitus, mucus, semen, tears, milk, water, and feces.

15. The diaper cover of claim 13 wherein said battery means comprises at least one pair of electrodes, each electrode comprising a different metal, said different metal electrodes producing sufficient voltage between them in the presence of said electrolyte solution to initiate said signal means.

16. The diaper cover of claim 1 wherein said fastening means comprise snap means.

17. The diaper cover of claim 16 wherein said power interrupt means comprises electrically conductive material bridging a pair of snap means and fastened to said diaper cover, thereby completing a circuit when said power interrupt means is fastened to said diaper cover.

18. The diaper cover of claim 1 wherein said housing means includes a water resistant surface between said fastening means.

19. The diaper cover of claim 1 wherein said wetness sensing means comprises a preprogrammed semiconductor chip means.

20. The diaper cover of claim 17, wherein said power interrupt means is placed within said diaper cover, the inward side of said power interrupt means being connected to said internally positioned spaced electrical contacts, the outward side of said power interrupt means being connected to snap means positioned on the external surface of said diaper cover, said snap means adapted for receiving complimentary snap means on said housing.

* * * * *